United States Patent [19]

Sogli et al.

[11] Patent Number: 5,750,682
[45] Date of Patent: May 12, 1998

[54] GLUTARYL 7-ACA DERIVATIVES AND PROCESSES FOR OBTAINING THEM

[75] Inventors: Loris Sogli, Novara; Davide Longoni, Gorgonzola; Giovanni Pozzi, Besana Brianza; Enrico Siviero, Pavia; Daniele Mario Terrassan, Concorezzo; Ermanno Bernasconi, Caronno Varesino, all of Italy; Francisco Salto, Madrid, Spain

[73] Assignee: Antibioticos S.p.A., Milan, Italy

[21] Appl. No.: 605,135

[22] PCT Filed: Jul. 17, 1995

[86] PCT No.: PCT/EP95/02802

§ 371 Date: Mar. 13, 1996

§ 102(e) Date: Mar. 13, 1996

[87] PCT Pub. No.: WO95/35020

PCT Pub. Date: Dec. 28, 1995

[30] Foreign Application Priority Data

Apr. 21, 1995 [IT] Italy .................. MI95 A 000823
Jul. 22, 1997 [IT] Italy .................. MI94A1562

[51] Int. Cl.⁶ .......................................... C07D 501/60
[52] U.S. Cl. .............................. 540/215; 540/230
[58] Field of Search .............................. 540/230, 215

[56] References Cited

U.S. PATENT DOCUMENTS

| | | | |
|---|---|---|---|
| 3,658,649 | 4/1972 | Arnold et al. | 195/29 |
| 4,275,062 | 6/1981 | Breuer et al. | 424/246 |
| 4,558,123 | 12/1985 | McShane | 544/16 |
| 5,095,107 | 3/1992 | Blanchard | 540/205 |
| 5,229,509 | 7/1993 | Nieves Elvira et al. | 540/218 |
| 5,424,196 | 6/1995 | Cambiaghi et al. | 435/51 |
| 5,571,910 | 11/1996 | Walker et al. | 540/230 |

OTHER PUBLICATIONS

Matsumoto, K. et al *Chemical Abstract* No. 88:119418, The Abstract of JP 52125696 (Oct. 21, 1977), Obtained Via STN (1978).

Carey, F. A. et al. *Advanced Organic Chemistry, Part A: Structure and Mechanisms* (Plenum Press, N.Y.) pp. 258, 259 and 286 (1990).

Greene, T.W. *Protective Groups in Organic Synthesis* (Wiley & Sons, N.Y.) pp. 152-157 173 and 174 (1981).

Greene, T.W. et al. *Protective Groups in Organic Synthesis* (Wiley & Sons, N.Y.) pp. 224-226, 253 and 254 (1991).

Krempova, A. et al. *Chemical Abstract* No. 111:170083, The Abstract of CS 251457 (Aug. 15, 1988) Obtained Via STN (1989).

*Primary Examiner*—Mukund J. Shah
*Assistant Examiner*—King Lit Wong
*Attorney, Agent, or Firm*—Oblon, Spivak, McClelland, Maier & Neustadt, P.C.

[57] ABSTRACT

There are disclosed new compounds of formula (I), wherein R is: a hydrogen atom: a linear or branched C1–C4 alkyl group, unsubstituted or substituted by at least a phenyl group or at least a hydrogen atom: a benzyl group substituted by at least a linear or branched C1–C4 alkyl or alkoxy group or a nitro group; a silyl substituted by at least a linear or branched, unsubstituted or substituted C1–C4 alkyl group; n is 0 or 1; and Y is a radical of formula (II), wherein A is H, OH, Cl, CH2, CH2X, where X is F, Cl, Br, I, OH or OR' and R' is COCH3 or a linear or branched, unsubstituted or substituted C1–C4 alkyl group and ... represents a single or a double bond, with the proviso that when n=0 and R is H, R' is not a methyl group; and processes for obtaining them.

5 Claims, No Drawings

GLUTARYL 7-ACA DERIVATIVES AND PROCESSES FOR OBTAINING THEM

This is a §371 application of PCT/EP95/02802, filed Jul. 17, 1995.

The present invention relates to new cephalosporin intermediates, particularly to new 7-β-glutarylamido cephalosporins and to processes for obtaining them, useful for the preparation of therapeutically, important cephalosporinic antibiotics.

It is well known that the major part of semisynthetic cephalosporins is obtained from 7-aminocephalosporanic acid (7-ACA) by acylation reactions of the amino group in 7 and by nucleophilic substitution of the acetoxy group in 3'. 7-ACA is still industrially produced by chemical hydrolysis of cephalosporin C through a complicated process which involves reagents and solvents very toxic and polluting and extreme working conditions.

Enzymatic or chemical-enzymatic processes by glutaryl 7-ACA have been lately developed to overcome these shortcomings. Said processes provide two steps, in the first step cephalosporin C is transformed enzymatically in an aqueous medium in glutaryl 7-ACA, by oxidative deamination with D-aminoacid oxidase [(BE-A-736934 (Glaxo); JP-A-40588 (Asahi); EP-A-0496993 (Antibioticos)], or chemically, by oxidative transamination [U.S. Pat. No. 4079180 (Asahi)]. The glutaryl 7-ACA is then deacylated by the glutaryl 7-ACA acylase enzyme [JP-A-186599 (Asahi); EP-A-0496993 (Antibioticos)].

7-ACA cannot be used per se for the syntheses of the latest cephalosporins, for instance the 3-alkenyl-ones (Cefprozil, Cefdinir), and the quaternary 3'-ammoniummethyl ones (Cefepime), but it has to be first undergone to protection reactions of the amino group (for instance by acylation or transforming it in a Schiff's base) and of the carboxy group (for instance by esterification). Besides, using 7-ACA is expensive for preparing specific cephalosporins such as the 3-cephem-3-halo substituted (for instance Cefaclor) or the unsubstituted ones (norcephalosporins, for instance Ceftizoxime and Ceftibuten), and the industrial processes known hitherto for the production thereof use, as starting materials, compounds containing the penicillinic core, for instance penicillin G or V, and come to obtaining the desired final products by a complicated sequence of chemical reactions which may provide, subsequently, protecting of carboxyl, sulfoxidation, the opening of the penicillanic ring, the rearrangement to cephalosporanic ring, etcetera. See, at this purpose, U.S. Pat. No. 4,052,387, U.S. Pat. No. 4,075,203, U.S. Pat. No. 4,081,440, U.S. Pat. No. 4,153,72, U.S. Pat. No. 4,031,084 and U.S. Pat. No. 4,346,218.

It is apparent that the glutaryl 7-ACA is not only cheaper than 7-ACA but it shows a variety of advantages, from a chemical-synthetic point of view, in respect with 7-ACA and cephalosporin C itself, the latter being sometimes used to produce cephalosporinic antibiotics. Yet, isolating glutaryl 7-ACA, given its high water solubility, is technically hard and expensive.

Other 7-ACA derivatives such as the known halomethyl derivatives, for instance the 3-chloroismethyl or 3-bromomethyl derivatives, are obtained from 7-ACA by a complicated sequence of protection reactions of the amino and carboxy groups, or by esters-sulfoxides of penicillin G by sophisticated technologies (opening of the penicillinic ring, electrochemical chlorinating, rearrangement to cephalosporinic ring).

Also the 3-exomethylene-derivatives of 7-ACA have a key structure for obtaining important cephalosporinic antibiotics. A few methods are known for transforming cephem derivatives into 3-exomethylene cepham derivatives.

These methods require the use of harmful and toxic compounds of Cr (II) (J. Chem. Soc. Chem. Comm. 800, 1972) or the utilize of electrochemical reductions, expensive and technologically complicated (Torii et al. Bull. Chem. Soc. Jpn. 59, 3975, 1986) starting from 3-acetoxymethyl or 3-halomethyl cephem, respectively.

There are other procedures which utilize Zn, as a reducing agent, yet starting from more expensive 3-thiofunctionalized derivatives.

The present invention relates to compounds having the following general formula (I)

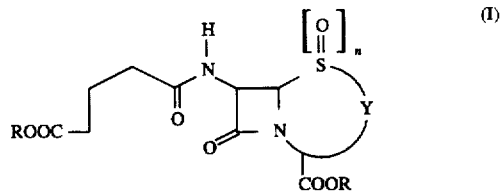

wherein R is:
- a hydrogen atom;
- a linear or branched $C_1$–$C_4$ alkyl group, unsubstituted or substituted by at least a phenyl group or at least a hydrogen atom;
- a benzyl group substituted by at least a linear or branched $C_1$–$C_4$ alkyl or alkoxy group or a nitro group;
- a silyl substituted by at least a linear or branched, unsubstituted or substituted $C_1$–$C_4$ alkyl group;

n=0 or 1; and Y is a radical of formula

wherein A is H, OH, Cl, $CH_2$, $CH_2X$, where X is F, Cl, Br, I, OH or OR' and R' is $COCH_3$ or a linear or branched, unsubstituted or substituted $C_1$–$C_4$ alkyl group and ⟿ represents a single or a double bond, with the proviso that when n=0 and R is H, R' is not a methyl group.

The compounds of formula (I), as above defined, are new cephalosporinic intermediates useful for preparing cephalosporinic antibiotics.

In The compounds of formula (I) as above defined, wherein R is a hydrogen atom, a methyl, ethyl, propyl, t-butyl, 2,2,2-trichloroethyl, diphenylmethyl, 4-nitrobenzyl, 4-methoxybenzyl, 3,4-dimethoxybenzyl, trimethylsilyl and triethylsilyl group, are preferred.

The glutaric side chain is a protecting group very good for the 7-ACA amino group; in fact, on said chain, there is no group which can interfere with the subsequent reactions, such as, for instance, the amino group of the aminoadipic chain of the cephalosporin C. The glutaric side chain per se allows to stabilize the cephalosporinic core and to carry out the functionalizing of the position 3 at best. It is generally necessary instead, to protect the amino group, in the case of 7-ACA, to carry out the functionalizing of the position 3.

Besides, the absence of interfering groups on the glutaric chain greatly helps the chemical cut of said chain in the final stage of the process for producing a certain antibiotic and, depending on the type of the antibiotic, said chain can be predictably removed, in a simpler way, enzymatically.

Another subject of the present invention is a process for obtaining the compounds of formula (I), as above defined, wherein R and Y are as above defined, which comprises the enzymatic hydrolysis of the glutaryl 7-ACA, or the corresponding sulfoxide, in an aqueous solution, as it is obtained from the enzymatic reaction of the oxidative deamination of cephalosporin C, for obtaining the corresponding desacetyl glutaryl 7-aminocephalosporanic acid, the subsequent extractive esterification, and, optionally, the oxidation of the resulting diester, thus obtaining the corresponding 3-cephem diester, or the diester-sulfoxide, of formula (I), as above defined, wherein A=$CH_2X$, wherein X is OH or directly esterifying the glutaryl 7-ACA, or the corresponding sulfoxide, thus obtaining the corresponding 3-cephem diester, or the diester-sulfoxide, of formula (I), as above defined, wherein A=$CH_2X$, and X is OR' and R' is $COCH_3$; if desired, transforming the 3-hydroxymethyl cephem derivatives into the compounds of formula (I), wherein A=–$CH_2X$ and X is F, Cl, Br or I, by halogenating, working in an anhydrous environment; or X=–OR', wherein R' is a $C_1$-$C_4$ alkyl, as above defined, by etherifying; the resulting halomethyl- and acetoxymethyl-derivatives, if desired, may be transformed, respectively, by reductively dehalogenating and deacylating, into the corresponding 3-exomethylene cepham derivatives, if desired, transforming the compounds of formula (I) so obtained into the corresponding 3-hydroxy-3-cephem derivatives of formula (I), wherein A=OH, and n=0 or 1, by ozonolysis.

The following reaction schemes show some preferred examples of the process for obtaining the compounds of general formula (I). (DPM=diphenylmethyl).

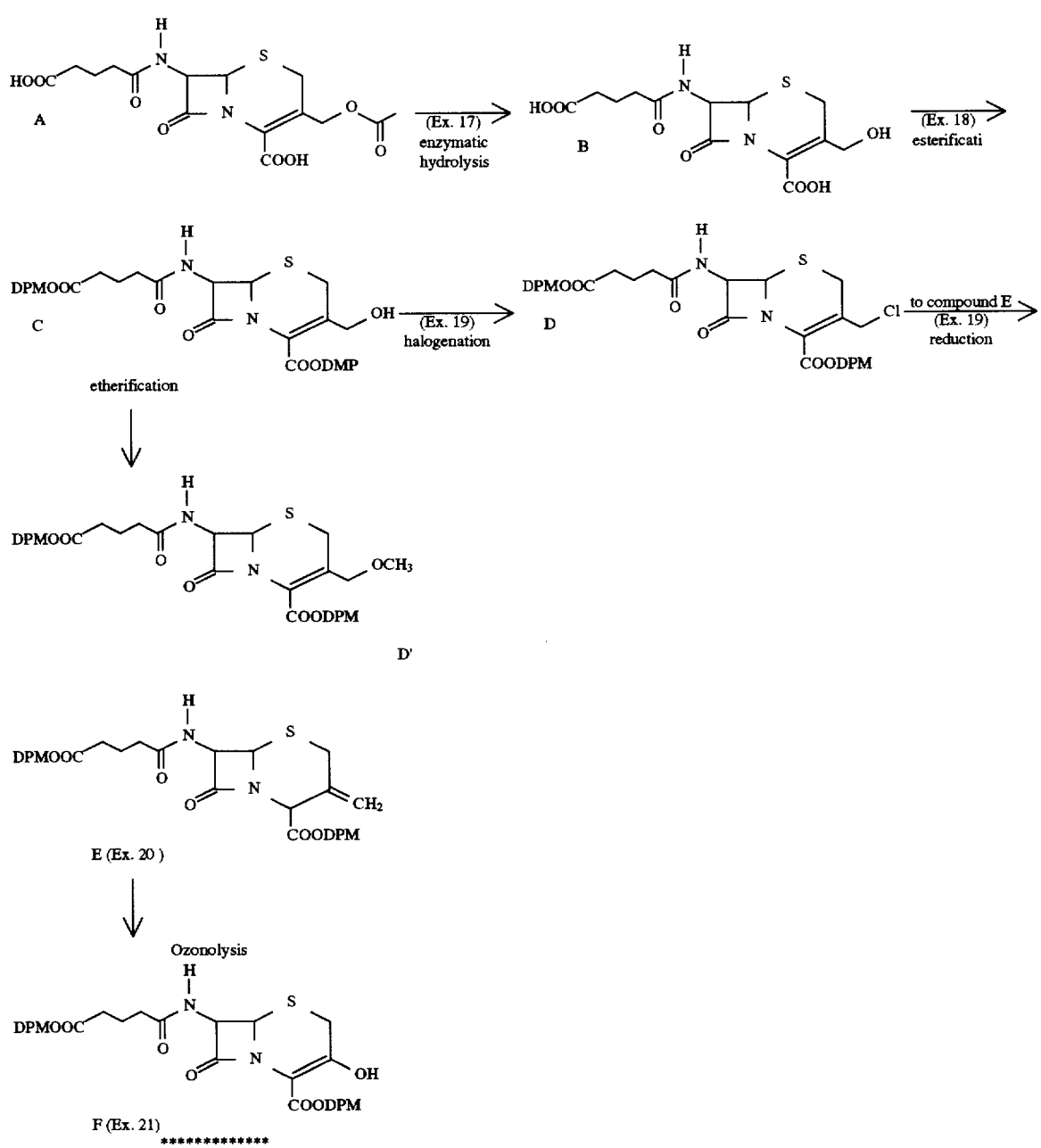

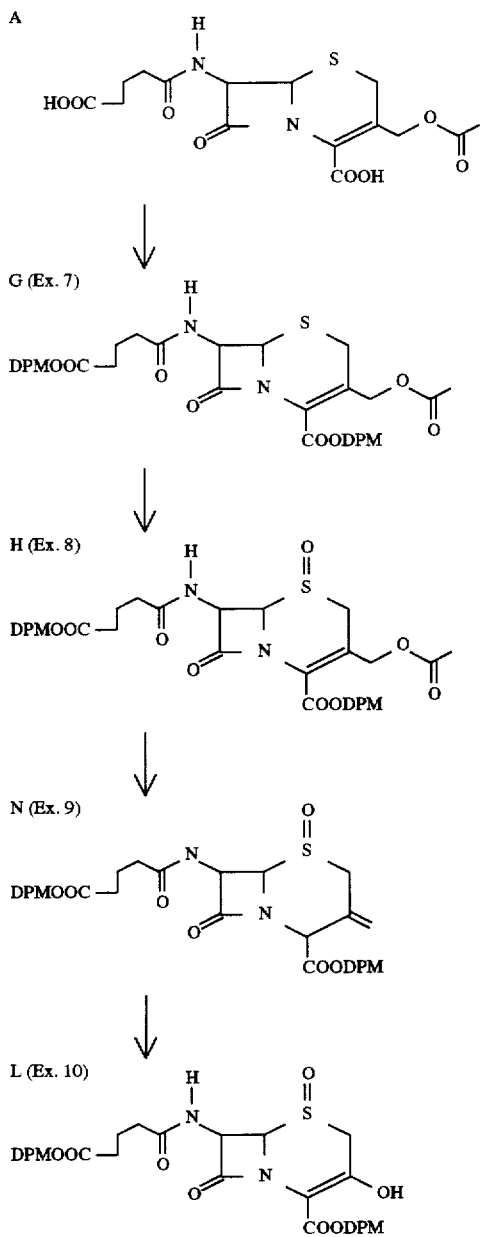
Said diester of glutaryl 7-ACA may also be optionally reduced directly to 3-exomethylene cepham as it is illustrated in the following reaction scheme which is preferred embodiment:
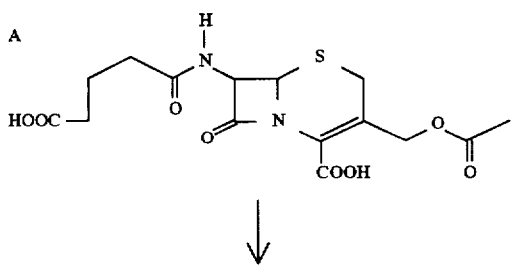
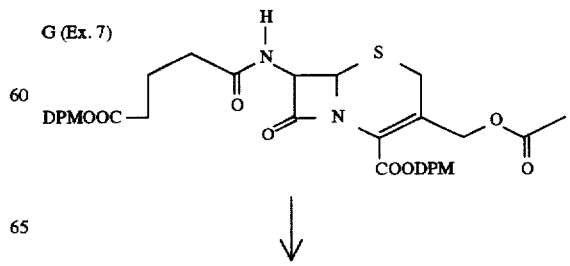

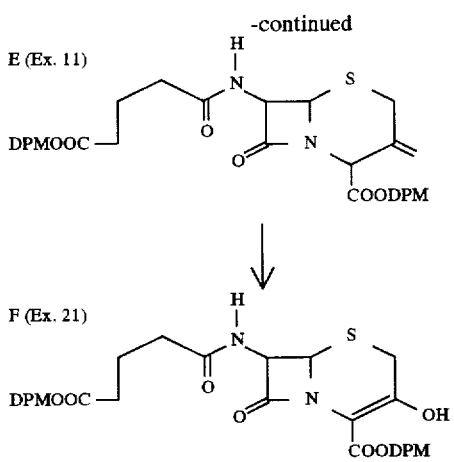

The enzymatic hydrolysis reaction is carried out on an aqueous solution of the compound A in the presence of the acetylesterase enzyme, maintaining the pH between 7 and 8, at room temperature; the time necessary to complete the reaction ranges between 80 minutes and 2 hours.

The extractive esterification reaction is carried out directly on the aqueous solution of the desacetylglutaryl 7-ACA acid (B) coming from the preceding step using diphenyldiazomethane dissolved in an organic solvent, immiscible or poorly miscible in water, maintaining the pH of the mixture between 2.5 and 5 and the temperature between −10° C. and 25° C.

Besides to diphenyldiazomethane (obtained for instance by oxydation of the benzophenone hydrazone), 4-nitrobenzylchloride, 4-methoxy-benzylchloride, 4-nitrobenzylbromide, 4-methoxy-benzylbromide and the like, can be used as esterifying agents.

The organic solvents which can be used are ethyl acetate, methyl acetate, toluene, methylene chloride, methylisobutylketone, methylethylketone and dimethylcarbonate. The time necessary to complete the reaction ranges between 4 and 12 hours.

The halogenation of the desacetylglutaryl diester (C) is carried out in an anhydrous solvent in the presence of a halogenating agent at a low temperature. Suitable halogenating agents can be phosphorous halogenides such as, for instance, phosphorous trichloride, phosphorous pentachloride, phosphorous tribromide, and thionyl chloride. Suitable solvents can be dimethylcarbonate, methylene chloride and chloroform.

The temperatures range between −40° C. and 0° C., preferably −30° C. The time needed to complete the reaction ranges between 30 minutes and 2 hours.

The reductive dehalogenation and deacylation of the halomethylglutaryl diester (D) and of the acetoxymethylglutaryl diesters (G and H), respectively, are generally carried out with zinc, activated before use, in the presence of a proton source and of a free base complexing agent, in an inert solvent, within a temperature range that goes between −50° C. and 0° C.

As a reducing metal, zinc in powder, activated by treatment with acids such as, for instance, 3% hydrogen chloride, is preferred, followed by a washing with water or with an organic solvent, preferably with the solvent used for the reduction.

The solvents used are N,N-dimethylformamide, N,N-dimethylacetamide, N-methylformamide, dimethylsulfoxide.

Inorganic acids ammonium salts such as, for instance, ammonium chloride and ammonium bromide, are used as the proton source.

The presence of ammonia into the reaction mixture causes the isomerization of 3-exomethylenecepham into 3-methylcephem; it is therefore convenient to add a free base complexing agent to the reaction mixture. The complexing agents mostly used are zinc chloride, zinc bromide, ferrous trichloride.

The preferred temperature range goes from −50° C. to −30° C. The time needed to complete the reaction goes from 3 to 6 hours.

The ozonolysis reaction is carried out by passing ozone through a solution of the glutaryl 3-exomethylene cepham diester (E), or the corresponding diester sulfoxide (N), in an inert solvent at a temperature between −80° C. and 0° C.

Suitable solvents are the ones in which the glutaryl exomethylene cepham diesters are soluble.

The solvents used are methanol, ethanol, methyl acetate, ethyl acetate, methylene chloride, chloroform and mixtures thereof.

The preferred temperature range is between −80° C. and −50° C. The double bond of the exomethylene derivative rapidly reacts with ozone to form an ozonide intermediate in situ. The ozone excess is removed making a nitrogen or oxygen stream pass through the reaction mixture, when the ozonide forming is complete. The ozonide is decomposed using reducing agents selective for the group such as, for instance, sodium bisolfite, sulfur dioxide, trimethylphosphite, triethylphosphite to give the glutaryl 3-hydroxy-3-cephem diester (F) and the corresponding diester sulfoxide (L). The reducing agent, used in excess, is added to the reaction mixture at a temperature between −80° C. and 0° C. The suspension is left under stirring until a negative response to the test potassium iodide-soluble starch, is obtained.

It has to be noticed that the aqueous solution of the glutaryl 7-ACA, as it is obtained from the enzymatic reaction of oxidative deamination of the cephalosporin C. is directly used for obtaining glutarylcephalosporins which is the subject of the present invention.

In fact, to obtain the compounds object of the present invention, the isolation of the glutaryl 7-ACA is not necessary because the first changes which have to be effected to the molecule are carried out in an aqueous environment.

Besides, the organic solution of the glutaryl diester, obtained by extractive esterification, can be used as such for the subsequent reactions or it can be evaporated, obtaining the crystalline glutaryl diester which can be used for other reactions and in different solvents.

It has been further found that, differing from glutaryl 7-ACA and desacetylglutaryl 7-ACA, the glutaryl diesters of general formula (I) are soluble in the organic solvents commonly employed in synthesizing the cephalosporinic antibiotics, such as, for instance, methylene chloride, ethyl acetate, acetone, etc.

This peculiarity is extremely important from a synthetic point of view, particularly when reactions in an anhydrous environment have to be carried out.

The haloderivatives of formula (I) obtained carrying out the process of the invention, are particularly useful for obtaining various cephalosporinic antibiotics such as, for instance, the ones of the last generations, such as the 3-alkenyl cephalosporins, which are obtained by a Wittig reaction; the 3'-ammonium methyl cephalosporins, obtained by quaternising with heterocyclic bases or the 3-exomethylene cepham derivatives (intermediates for Cefaclor, 3-norcephalosporins, etc.), among which, the compounds of formula (I) wherein A=$CH_2$ obtained by reductive dehalogenation.

Also the 3-hydroxy derivatives, obtained by ozonolysis from the exomethylene derivatives of formula (I), carry to the core of Cefaclor by subsequent chlorination, or to the core of 3-norcephalosporins (Ceftibuten, Ceftizoxime, etc.) after eliminating the hydroxy group.

A further subject of the present invention is a process for obtaining the 3-cephem derivatives of formula (I), as above defined, wherein A=Cl, which comprises the chlorinating of glutaryl 3-hydroxycephem diester of formula (I), as above defined, wherein A=OH, in the presence of an aprotic polar solvent, the hydrolysis of the two carboxy groups of the resulting glutaryl 3-chloro-3-cephem diester, in the presence of a Lewis acid, at a temperature comprised between the room temperature and 50° C. and the deacylation of the glutaryl 3-chloro-3-cephem-4-carboxylic acid so obtained.

The deacylation of said glutaryl 3-chloro-3-cephem-4-carboxylic acid may be carried out both chemically and enzymatically to obtain the corresponding 7-β-amino-3-chloro-3-cephem-4-carboxylic acid which, in its turn, may be suitably functionalized to obtain Cefaclor.

The following scheme shows a preferred embodiment of the inventive process just above described.

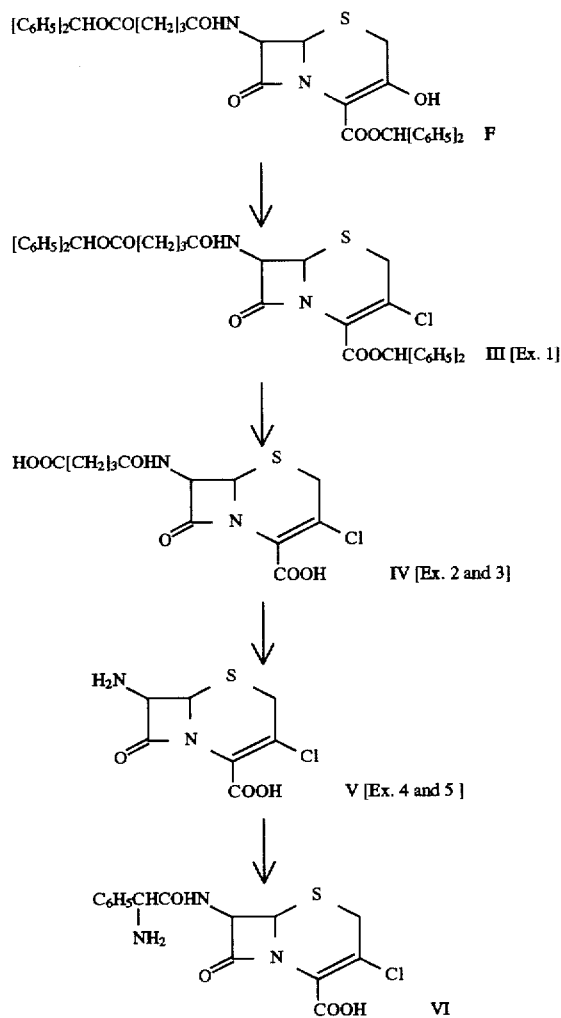

The chlorination of the glutaryl 3-hydroxy-3-cephem diester (F) is carried out in N,N-dimethylformamide in the presence of a chlorinating agent at room temperature. As a chlorinating agent, phosphorous trichloride and pentachloride, thionyl chloride, oxalyl chloride and fosgene may be mentioned.

It is preferable to use co-solvents such as dimethyl sulfoxide, tetrahydrofuran, dioxane, methylene chloride, dimethylacetamide. The reaction is completed within 2–4 hours.

Generally, the chlorination of the glutaryl 3-hydroxy-3-cephem diester of formula (I), as above defined, wherein A=OH, is also carried out in an anhydrous aprotic solvent, in the presence of a triarylphosphite-chlorine complex and of a base. Suitable solvents are chloroform, methylene chloride, and tetrahydrofuran.

The preferred chlorinating agent is the triarylphosphite-chlorine complex. Pyridine, quinoline and N,N-dimethylaniline are used as a base. The reaction is carried out within a temperature range going from –30° to +30° C. and preferably at –15° C.

The deprotection of the two carboxy groups of the glutaryl 3-chloro-3-cephem diester (III) is carried out in anisole, in the presence of a Lewis acid, heating at 30°–50° C. Among the suitable Lewis acids, there are aluminum trichloride, boron trifluoride and trifluoroacetic acid. As a solvent, also phenol may be used.

The hydrolysis of the diesters may also be carried out in formic acid heating at 40°–50° C. The time needed to complete the reaction is 1–3 hours.

The deacylation of the glutaryl 3-chloro-3-cephem-4-carboxylic acid (IV) may be carried out both chemically and enzymatically. The chemical deacylation (via iminochloride-iminoether) contemplates using an anhydrous inert solvent, an alkylchlorosilane, a base (scavenger of the developing hydrogen chloride), a phosphorous halogenide and an alcohol, at a temperature between –50° C. and –15° C.

As a solvent, methylene chloride, chloroform and carbon tetrachloride, are used. The alkyl chlorosilanes used are dimethylchlorosilane, trimethylchlorosilane and triethylchlorosilane. As a base, dimethylamide, triethylamine, pyridine and N,N-dimethylaniline are used. Suitable halogenides are, for instance, phosphorous trichloride and pentachloride.

As an alcohol, methanol, ethanol, propanol, butanol and isobutanol, are used. The time needed to complete the reaction is 2–4 hours. The enzymatic deacylation is carried out on an aqueous solution of the compound IV, in the presence of an acylase enzyme such as, for instance, the glutaryl 7-ACA acylase, maintaining the pH between 7.5 and 9.0 at room temperature. The time needed to complete the reaction is 30 minutes–2 hours.

Another subject of the present invention is a process for obtaining the 3-cephem derivatives of formula (I), as above defined, wherein A=Cl, which comprises the reduction of sulfoxide and the chlorination in a single step, in the presence of an aprotic solvent, of the 3-cephem derivatives of formula (I), as above defined, wherein A=OH and n=1, to give the corresponding 3-chloro derivative. The compounds so obtained can be used for the production of important antibiotics by known methods (U.S. Pat. No. 3,925,372), particularly by the subsequent deprotection in 7 and 4 to obtain the corresponding 7-β-amino-3-chloro-cephem ester as its halohydrate and the 7-β-amino-3-chloro-3-cephem-4-carboxylic acid, respectively.

The following reaction scheme shows a preferred embodiment of the process just above described.

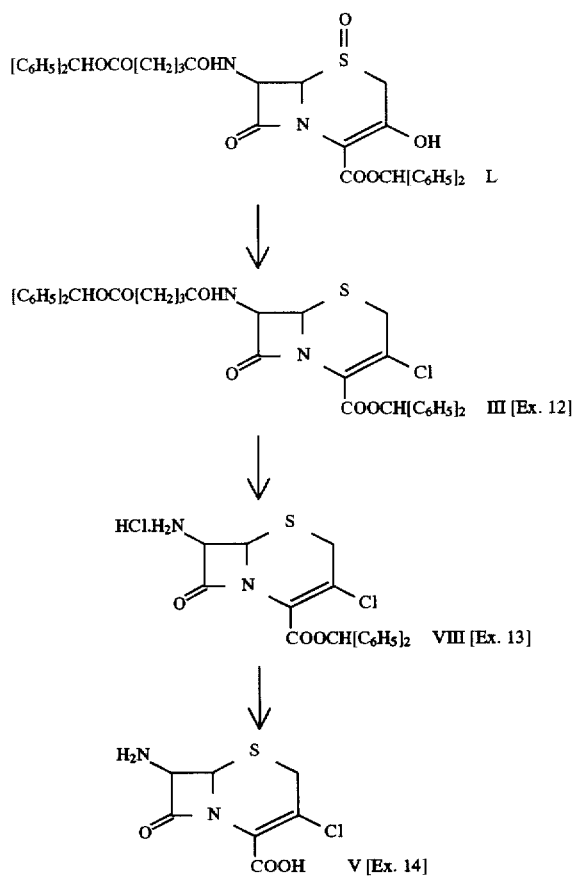

If desired, the deprotection can also be effected simultaneously halogenating in 3 and deprotecting in 7, thus obtaining the corresponding 7-β-amino-3-chloro-3-cephem ester halohydrate and by subsequent deprotection in 4, the corresponding 7-β-amino-3-chloro-3-cephem-4-carboxylic acid.

The following reaction schemes show some preferred embodiments of the processes just above described.

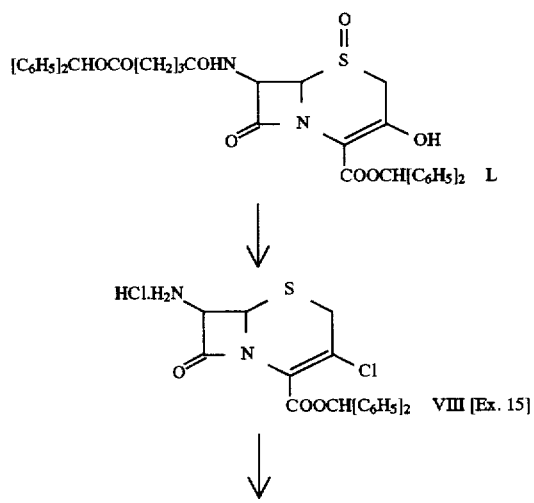

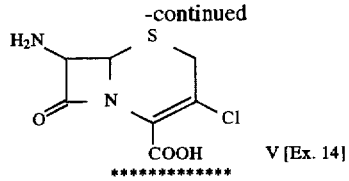

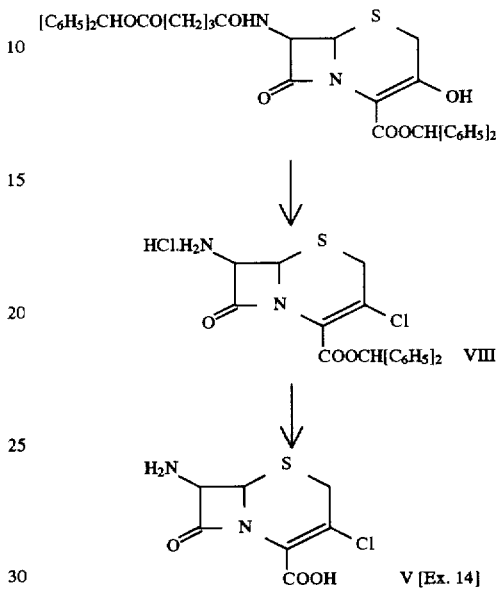

The chlorination/reduction of the 3-hydroxy-3-cephem derivatives of formula (I), wherein n=1, is carried out in N,N-dimethylformamide in the presence of a chlorinating/reducing agent at room temperature.

The preferred chlorinating/reducing agent is phosphorous trichloride.

It is possible to use cosolvents such as dimethylsulfoxide, tetrahydrofuran, dioxane, methylene chloride, dimethylacetamide. The time needed to complete the reaction is 2–4 hours.

The chlorination/reduction of the 3-hydroxy-3-cephem of formula (I), wherein n=1, is also carried out in an aprotic anhydrous solvent in the presence of a triarylphosphite-chlorine complex and a base. Suitable solvents are chloroform, methylene chloride and tetrahydrofuran. The preferred chlorinating agent is the triphenylphosphite-chlorine complex. As a base, pyridine, quinoline, and N,N-dimethylaniline, are used. The reaction is carried out at a temperature range between −30° and +30° C. and preferably from −15° C. The reaction is completed in 0.5–2 hours.

A further subject of the present invention is a process for obtaining the 3-hydroxy-3-cepham of formula (I), as above defined, wherein A=OH and n=0, which comprises the reduction of the glutaryl 3-hydroxy-3-cephem diester of formula (F), as above defined, and, if desired, dehydrating the resulting 3-hydroxy-3-cepham derivative to obtain the corresponding 3-cephem of formula (I), as above defined, wherein A=H and n=0.

The following reaction scheme shows a preferred example of the process just above described.

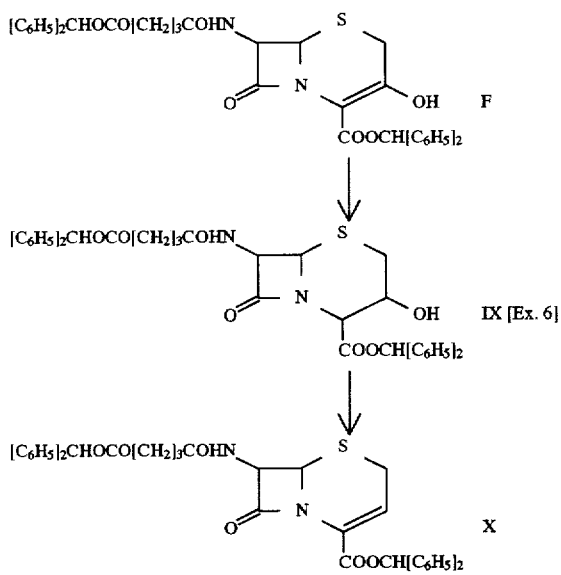

The following examples are merely meant to illustrate the present invention, yet not limiting it in any way. The ¹H-NMR spectra were recorded by a 300 MHz Brucker spectrometer.

The abbreviations used in the description of the ¹H-NMR spectra mean: s=singlet; d=doublet; dd=double doublet; t=triplet, q=quadruplet; m=multiplet; brs=broad singlet. The chemical shifts are reported in ppm.

The MS spectra were recorded by a spectrometer VARIAN MAT 311 A. Ozone generator: Fisher OZON 502. All of the syntheses steps were followed kinetically by HPLC chromatographic analysis using a Shimadzu HPLC LC-10AD endowed with a Brownlee RP18 column, a Shimadzu SPD-6A detector and a Shimadzu C-R4A integrator.

EXAMPLE 1

Preparation of the diphenylmethyl 7-β-[(4-diphenylmethoxycarbonyl)-butanamido]-3-chloro-3-cephem-4-carboxylate (III).

6.73 g of phosphorous trichloride (0.048 mol) were slowly added to a cooled solution (water/ice bath) of 13.25 g of the compound (F), (0.02 mol) in 110 ml of N,N-dimethylformamide, maintaining the temperature lower than 5° C.

The transformation of the product (F) is followed by HPLC. The reaction mixture was left under stirring at room temperature, for 4 hours and then poured in 75 ml of an aqueous solution of hydrogen chloride at 5%, maintaining the temperature lower than 10° C.

The suspension was extracted with ethyl acetate (2×100 ml) and the collected organic extracts were rinsed with an aqueous solution of 5% hydrogen chloride (50 ml), followed by a buffer at pH 6.5 (100 ml). The organic phase was dried ($Na_2SO_4$) and the solvent was evaporated to dryness under reduced pressure.

The title product, recovered from the oily residue by crystallisation with methanol, was a slightly yellow chrystalline powder (8.60 g, 0.12 mol) having a HPLC purity of 95%. The molar yield, calculated on the basis of the HPLC title, was 60% on the recovered product.

¹H-NMR ($CDCl_3$, 300 MHz)

1.97(m, 2H, —$CH_2$—); 2.24 (t, 2H, —$CH_2$—); 2.48 (t, 2H, —$CH_2$); 3.41–3.71 (ABq, 2H, J=17.0 Hz, C2); 4.98 (d, 1H, J=5.0 Hz, C6); 5.81(dd, 1H, J=5.0–9.0 Hz, C7) 6.45 (d, 1H, J=9.0 Hz, NH); 6.89–6.99 (s, 2H, diphenylmethyl-CH); 7.23–7.45 (brs, 20 H, aromatic).

Elemental analysis for the product (III) $C_{38}H_{33}N_2O_6ClS$: calculated (%): C, 67.00; H, 4.88; N, 4.11; Cl, 5.20; S. 4.70 found (%): C, 66.66; H, 5.07, N, 4.08; Cl, 4.80; S, 4.66.

The mass spectrum ("Field Desorption" technique) showed a molecular peak at 680, which agrees with the molecular weight calculated for $C_{38}H_{33}N_2O_6ClS$.

EXAMPLE 2

Preparation of the 7-β-(4-carboxybutanamido)-3-chloro-3-cephem-4-carboxylic acid (IV).

A solution of 14.34 g of the product (III) (0.2 mol, HPLC purity 95%) in 200 ml of anisole was added to a solution of 6.49 g of anhydrous aluminum trichloride (0.047 mol) in 80 ml of anisole, maintaining the temperature lower then 30°–35° C. for 2 hours. The transformation of the product (III) was followed by HPLC technique. The reaction mixture, after cooling at −10° C., was poured into 100 ml of a cool solution of 2% HCl, maintaining the temperature lower than 15° C. The aqueous acid phase was saturated with sodium chloride and extracted with ethyl acetate (3×100 ml). The collected organic extracts were concentrated by evaporating the solvent till the crystallisation of the product IV was obtained.

The title product was a slightly yellow, microcrystalline solid (5.50 g, 0.015 mol) having a HPLC purity higher than 95%. The molar yield, calculated on the basis of the HPLC title, was 75% on the recovered product.

¹H-NMR (DMSO, 300 MHz)

1.72 (m, 2H, —$CH_2$—); 2.22 (m, 4H, —$CH_2$—); 3.69–3.98 (ABq, 2H, J=18.0 Hz, C2); 5.18(d, 1H, J=4.6 Hz, C6); 5.67 (dd, 1H, J=4.6–8.0 Hz, C7); 8.95 (d, 1H, J=8.0 Hz, NH). Analysis-Calculated for $C_{12}H_{13}ClN_2O_6S$: C, 41.33; H, 3.76; Cl, 10.16; N, 8.03. Found: C, 41.80; H, 3.89; Cl, 9.80; N, 7.79.

The mass spectrum (FAB mass spectrum) showed the protonated molecular ion at m/z 349, which agrees with the molecular weight calculated for $C_{12}H_{13}ClN_2O_6S$.

EXAMPLE 3

Preparation of the 7-β-(4-carboxybutanamido)-3-chloro-3-cephem-4-carboxylic acid (IV).

A solution of 14.34 g of the product (III) (0.02 mol, HPLC purity 95%) in 70 ml of 99% formic acid was heated at 45° C. for 30 minutes. The acid excess was removed by evaporating at the same temperature. The product (IV) was then recovered from the residual oil by crystallisation from ethyl acetate.

The product was a slightly yellow microcrystalline solid (5.58 g, 0.016 mol) having a HPLC purity higher than 95%. The molar yield, calculated on the basis of the HPLC title, was 80% on the recovered product.

¹H-NMR (DMSO, 300 MHz)

1.72 (m, 2H, —$CH_2$—); 2.22 (m, 4H, —$CH_2$—); 3.69–3.98 (ABq, 2H, J=18.0 Hz, C2); 5.18(d, 1H, J=4.6 Hz, C6); 5.67 (dd, 1H, J=4.6–8.0 Hz, C7); 8.95 (d, 1H, J=8.0 Hz, NH).

EXAMPLE 4

Preparation of the 7-β-amino-3-chloro-3-cephem-4-carboxylic acid (V) (Chemical method)

To a suspension of 7.34 g of the product (IV) (0.02 mol, HPLC purity 95%) in 60 ml of anhydrous methylene chloride, cooled at 0° C., 9.10 g of N,N-dimethylaniline and 5.43 g of trimethyl chlorosilane were added, maintaining the temperature lower than 30° C. 5.20 g of phosphorous pentachloride (0.025 mol) were added to the solution cooled at −5° C. 16 ml of isobutanol were added very slowly maintaining the temperature lower than −20° C., after having maintained the reaction mixture under stirring for two hours at −40° C. 30 ml of water were added after an hour maintaining the temperature lower than 0° C. and the pH at the value of 7 by concentrated ammonia. The organic phase was removed and the product recovered from the aqueous phase by precipitation at the isoelectrical point (pH 3.9–4.0) using concentrated HCl to lower the pH. The precipitated solid was filtered, washed with methanol and dried.

The microcrystalline solid was recognized as the title product. The molar yield, calculated on the basis of the HPLC title, was 85% based on the recovered product. The data of the NMR spectra of the obtained product were coincident with the ones known in literature.

EXAMPLE 5

Preparation of the 7-β-amino-3-chloro-3-cephem-4-carboxylic acid (V) [Enzymatic method]

One liter of an aqueous solution of 25 mM $KH_2PO_4$ containing 15.0 g of the product (IV) (0.043 mol) was brought at pH 8 with 2% $NH_4OH$. The solution was thermostated.

The solution was thermostated at 25° C. and added with 10 g of the glutaryl 7-ACA acylase enzyme immobilized on a resin. The mixture was let under stirring for an hour maintaining the pH at the value of 8 by adding 2% $NH_4OH$. The enzyme was filtered and the product was recovered from the aqueous phase by precipitation at the isoelectrical point (pH 3.9–4.0), using concentrated HCl to lower the pH. The precipitated solid was filtered, washed with methanol and dried.

The microcrystalline solid was recognized as the title product. The molar yield, calculated on the basis of the HPLC title, was 90% on the recovered product. The data of the NMR spectrum of the resulting product were coincident with the ones known in literature.

EXAMPLE 6

Preparation of diphenylmethyl 7-β-[(4-diphenylmethoxycarbonyl)-butanamido]-3-hydroxy-cepham-4-carboxylate (IX).

A solution of 13.6 g of the product (F) (0.02 mol), 8.2 ml of glacial acetic acid, 50 ml of methanol and 150 ml of toluene, was cooled at −55° C., added with 1.85 g of sodium boron hydride (0.048 mol), the temperature was raisen up to −30° C. soon after the end of the addition. The cold reaction mixture was poured into 145 ml of a saturated solution of $NaHCO_3$, maintaining the temperature lower than 15° C. The organic phase was concentrated by evaporating the solvent till the crystallisation of the product (IX) was obtained.

The title product was a white microcrystalline solid (8.86 g, 0.012 mol) having a HPLC purity higher than 90%. The molar yield, calculated on the basis of the HPLC title, was 60% on the recovered product.

$^1$H-NMR (DMSO, 300 MHz)

1.96 (m, 2H, —$CH_2$—); 2.23 (t, 2H, —$CH_2$—); 2.48 (t, 2H, —$CH_2$—); 2.61–2.98 (AB of ABX, 2H, JAB=13.8 Hz, JBX=10.0 Hz, JAX=3.5 Hz, C2), (3.32 (d, 1H, J=7.8 Hz, OH); 4.08 (m, 1H, J=10.0–7.8–6.0 Hz, C3); 4.84 (d, 1H, J=6.0 Hz, C2); 5.07 (d, 1H, J=4.0 Hz, C6); 5.53 (dd, 1H, J=9.0–4.0 Hz, C7); 6.51 (d, 1H, J=9.0 Hz, NH); 6.87–6.92 (s, 2H, diphenylmethyl-CH); 7.23–7.40 (brs, 20 H, aromatic).

EXAMPLE 7

Preparation of diphenylmethyl 7-β-[(4-diphenylmethoxycarbonyl)-butanamido]-3-acetoxymethyl-3-cephem-4-carboxylate (G).

The procedure described below consists of extractively esterifying 7-β-[(carboxybutanamido]-3-acetoxymethyl-3-cephem-4-carboxylic acid and isolating the corresponding title diphenylmethyl ester. 29.0 g of an ethyl acetate solution of diphenyldiazomethane were added to 1 l an aqueous solution of 25 mM $KH_2PO_4$ containing 23 g of the 7-β-(4-carboxybutanamido)-3-acetoxymethyl-3-cephem-4-carboxylic acid (0.058 mol). The biphasic mixture was put under stirring, thermostating at 10° C. 18% HCl was slowly added dropwise till pH=3.5, maintaining such pH for 1.5 hours and then lowering it at pH=2.5, maintaining under stirring for 30 minutes. The phases were separated when the synthesis ended, the organic phase being treated with 500 ml of $H_2O$ and bringing at pH=7.5 by $Na_2CO_3$.

The phases were separated by rinsing the organic phase two times with 500 ml of a saturated solution of NaCl. The organic phase was dried with $Na_2SO_4$ and the solvent was eliminated under vacuum (40 torr) at 30° C. The oily crude product was collected with 300 ml of isopropanol and under stirring for 1 hour at room temperature. The product was recovered by filtration and undergone to a further purification treating it with 250 ml of 1,1-diethoxymethane and under stirring for 30 minutes at 25° C.

26.2 g of a white solid recognized as the title product, having a HPLC purity of 94%, were obtained.

$^1$H-NMR ($CDCl_3$-200 MHz)

2.02 ppm (s, 3H, $CH_3CO$); 1.90–2.10(m,2H—$CH_2$—); 2.26 ppm (t, 2H, —$CH_2$—); 2.52 ppm (t, 2H—$CH_2$—); 3.33 3.55 (ABq, 2H, J=18.6 Hz, C-2); 4.79–5.04 ppm (ABq, 2H, J=13.6 Hz, $CH_2$—$OCOCH_3$); 4.79 ppm (d, 1H, J=5 Hz, C-6); 5.85 ppm (dd, 1H, J=5.0–8.8 Hz C-7); 6.09 ppm (d, 1H, J=8.8 Hz, —NH); 6.90 ppm (s, 1H, -diphenylmethyl-CH); 6.96 ppm (s, 1H, diphenylmethyl-CH); 7.31–7.46 ppm (m, 20H aromatic).

EXAMPLE 8

Preparation of diphenylmethyl 7-β-[(4-diphenylmethoxycarbonyl)-butanamido]-3-acetoxymethyl-3-cephem-4-carboxylate-1-oxide (H). 25 g (0.031 mol) of the product (G) were dissolved in 300 ml of anhydrous $CH_2Cl_2$ maintaining the temperature at 18°–20° C. 7.1 ml of a 32% solution of peracetic acid were dropwise added within 5 minutes in the flask, maintaining the solution under stirring. The disappearance of the compound (G) was observed in HPLC after 15 minutes. The solvent was eliminated under vacuum (80 torr) and the crude residue was collected with 300 ml of ethyl acetate.

The resulting solution was washed two times with 300 ml of 8% $NaHCO_3$ solution: The phases were separated. Counterextracting with 200 ml of AcOEt was effected from the aqueous phase. The phases were separated. The organic phases were reunited and washed 2 times with 400 ml of a saturated solution of NaCl. The organic phase was concentrated to 250 ml and left at 0° C. After 8 hours the product was filtered and dried under vacuum at 30° C. for 4 hours.

21.1 g of the title product having a HPLC purity of 96% were recovered.

¹H-NMR (CDCl₃, 200 MHz)

2.03 ppm (s, 3H, CH₃CO); 1.97–2.08 ppm (m, 2H, —CH₂—); 2.31 ppm (t, 2H, —CH₂—); 2.52 (t, 2H, —CH₂—); 3.20–3.80 (ABq, 2H J=19.0 Hz, C-2); 4.46 ppm (d, 1H, J=4.8 Hz, C-6); 4.74–5.32 ppm (ABq, 2H, J=14.5 Hz, —CH₂—OCOCH₃); 6.11 ppm (dd, 1H, J=4.8 Hz, 9.9 Hz, C-7); 6.66 ppm (d, 1H, J=9.9 Hz, NH); 6.89 ppm ((s, 1H, diphenylmethyl-CH); 6.96 ppm (s, 1H, diphenylmethyl-CH); 7.26–7.50 ppm (m, 20H, aromatic).

EXAMPLE 9

Preparation of diphenylmethyl 7-β-[(4-diphenylmethoxycarbonyl)-butanamido]-3-methylene-cepham-4-carboxylate-1-oxide (N)

10 g of the (0.014 mol) of the compound (H) were dissolved in 100 ml of absolute DMF. This solution was dropwise added within 2 minutes to a flask containing a suspension of 18 g of activated Zn in powder, 30 g of NH₄Cl, 20 g of ZnCl₂ in 100 ml of absolute dimethylformamide, cooled at 0° C. Vigorous stirring was maintained for 6 hours at 0° C. The suspension was filtered and the solid residue was washed on the filter with 200 ml of ethyl acetate. The ethyl acetate used for washing was mixed with the filtrate obtaining the precipitation of an inorganic residue. The inorganic residue was filtered and 450 ml of H₂O were added to the resulting solution under stirring for 30 minutes. After filtering the biphasic mixture, the phases were separated and the organic phase was rinsed 2 times with 250 ml of a 18% solution of NaCl. Drying with Na₂SO₄, eliminating the solvent and crystallising the oily crude product in 200 ml of methanol leaving under stirring for 4 hours at room temperature and at 5° C. for 3 hours was effected.

The filtered product was dried in an oven under vacuum at 30° C. 6 g of a white solid, recognized as the title product, were recovered. HPLC purity=98.1%

¹H-NMR (CDCl₃ 200 MHz)

1;92–2.04 (m, 2H, —CH₂—); 2.25 ppm (t, 2H,—CH₂—); 2.48 ppm (t, 2H, —CH₂—); 3.36–3.62 ppm (Abq, 2H, C-2); 4.80 ppm (d, 1H, J=4.8 Hz, C-6) 5.32 ppm (s, 1H, C=CH₂); 5.42 (s, 1H, C=CH₂); 5.77 ppm (s, 1H, C-4); 5.92 ppm (dd, 1H, J=4.8 Hz–10.1 Hz, C-7); 6.85 ppm (d, 1H, J=10.1 Hz, NH); 6.83 ppm (s, 1H diphenylmethyl-CH); 6.87 ppm (s, 1H, diphenylmethyl-CH); 7.22–7.39(m, 20H, aromatic).

EXAMPLE 10

Preparation of diphenylmethyl 7-β-[(4-diphenylmethoxycarbonyl)-butanamido]-3-hydroxy-3-cephem-4-carboxylate-1-oxide (L).

In a solution of 13.54 g of the product N (0.02 mol) in 150 ml of ethylacetate, cooled at −65° C., ozone was insufflated for 25 minutes (about 1.3 mmol O₃/min).

The excess of ozone was removed insufflating oxygen for 5 minutes and nitrogen for 15 minutes. 7 ml of triethylphosphite (0.04 mol) were then added, maintaining the temperature lower than −50° C. At the end of the addition the solution gave a negative response to the peroxide test (KI-soluble starch).

The reaction mixture was poured in 50 ml of an aqueous solution of 5% HCl, after having allowed the temperature to raise up to −25° C., and left for 30 minutes under vigorous stirring at 15°–20° C. The organic phase was rinsed with 5% aqueous solution of sodium chloride (2×100 ml), dried with sodium sulfate and, after evaporating the solvent the residual oil was solidified by treatment with n-pentane.

The amorphous solid obtained was recognized as the title product. The molar yield, calculated on the basis of the HPLC title was 90% on the recovered product.

¹H-NMR (CDCl₃, 300 MHz)

2.02 (t, 2H, —CH₂—); 2.32 (t, 2H, —CH₂—); 2.52 (t, 2H, —CH₂—); 3.41+3.72 (ABq, 2H, J=19.0+1.0 Hz, C₂); 4.52 (dd, 1H, J=4.0+1.0 Hz, C₆); 6.03 (dd, 1H, J=4.0+10.0 Hz, C₇); 6.66 (d, 1H, J=10.0 Hz, NH); 6.89+6.92 (s, 2H, diphenylmethyl-CH); 7.20+7.40 (brs, 20 H, aromatic); 11.70 (s, 1H, OH).

EXAMPLE 11

Preparation of the diphenylmethyl 7-β-| (diphenylmethoxycarbonyl)-butanamido|-3-methylene-cepham-4-carboxylate (E).

A solution of 10 g of the product (G) (0.012 mol) in 100 ml of absolute dimethylformamide was added to a suspension of 15 g of activated Zn in powder, 12 g of NH₄Cl and 15 g of ZnCl₂ in 100 ml of absolute dimethylformamide cooled to 0° C. After 4 hours under vigorous stirring at 0° C. the suspension was filtered and the solid rinsed with 200 ml of ethyl acetate which were added to the filtrate. Filtering was effected again to eliminate the precipitated inorganic solid and 400 ml of H₂O were added to the resulting solution stirring for 30 minutes at room temperature.

The biphasic solution was filtered and, after separating, the organic phase was rinsed two times with 200 ml of a 18% solution of NaCl and dried over Na₂SO₄. The solvent was evaporated and the resulting oil was powdered from n-pentane. 6.2 g of light yellow solid recognized as the title product. HPLC purity=90%.

EXAMPLE 12

Preparation of diphenylmethyl 7-β-[ (diphenylmethoxycarbonyl)-butanamido]-3-chloro-3-cephem-4-carboxylate (III)

9.81 g of phosphorous trichloride (0.070 mol) were slowly added to a cooled solution (water bath/ice) of 13.54 g of the compound L (0.02 mol) in 110 ml of N,N-dimethylformamide, maintaining the temperature lower than −55° C. The reaction mixture was left under stirring at −55° C. for one hour and at room temperature for 4 hours; then it was poured in 75 ml of an aqueous solution of 5% hydrogen chloride, maintaining the temperature lower than 10° C. The suspension was extracted with ethyl acetate (2×100 ml) and the collected organic extracts were rinsed with an aqueous solution of 5% hydrogen chloride (50 ml) followed by a buffer at pH 6.5 (100 ml). The organic phase was dried (Na₂SO₄), and the solvent evaporated to dryness under reduced pressure.

The title product, recovered from the oily residue by crystallisation with methanol, was a light yellow crystalline solid (6.81 g, 0.012 mol) having a HPLC purity of 95%. The molar yield, calculated on the basis of the HPLC title, was 50% on the recovered product.

¹H-NMR (CDCl₃, 300 MHz)

1.97 (m, 2H, —CH₂—); 2.24 (t, 2H,—CH₂—); 2.48 (t, 2H, —CH₂—); 3.41–3.71 (Abq, 2H, J=17.0 Hz, C2); 4.98 (d, 1H, J=5.0 Hz, C6); 5.81 (dd, 1H, J=3.0–9.0 Hz, C7); 6.45 (d, 1H, J=9.0 Hz, NH); 6.89–6.99 (s, 2H, diphenylmethyl-CH); 7.23–7.45 (bis, 20H, aromatic).

EXAMPLE 13

Preparation of the diphenylmethyl 7-β-amino-3-chloro-3-cephem-4-carboxylate hydrochloride (VIII)

2.4 ml of pyridine and 6.0 g of phosphorous pentachloride were added to a solution of 13.62 g of the product III (0.020 mol) in 90 ml of methylene chloride, cooled at −15° C. The reaction mixture was cooled at −30° C. after having left it under stirring at −15° C., and added with 19 ml of isobutanol.

The title product was precipitated from the reaction mixture, brought back to −15° C., and left under stirring. The precipitated solid was filtered, rinsed with methylene chloride and dried. The obtained product was a white microcrystalline solid (6.12 g 0.014 mol); the $^1$H-NMR data were coincident with the ones of the true product, as reported in literature.

The molar yield, calculated on the basis of the HPLC title, was 70% on the recovered product.

EXAMPLE 14

Preparation of the 7-β-amino-3-chloro-3-cephem-4-carboxylic acid (V).

A solution of 8.75 g of the product VIII (0.02 mol) in 20 ml of 99% formic acid, was heated at 54° C. for 30 minutes. The acid excess was removed by evaporating at the same temperature, the residual oil was dispersed in 30 ml of water and the aqueous phase was rinsed with 30 ml of ethyl acetate (2×15 ml).

The product was recovered by precipitating at the isoelectrical point (pH 3,9–4,0) using concentrated ammonia to raise the pH. The precipitated solid was filtered, rinsed with methanol and dried. The product was a slightly yellow, microcrystalline solid (3.94 g, 0.0168 mol); the $^1$H-NMR data were coincident with the ones of the authentic product reported in literature.

EXAMPLE 15

Preparation of the diphenylmethyl 7-β-amino-3-chloro-3-cephem-4-carboxylate hydrochloride (VIII)

Chlorine gas was insufflated in a solution of 13.10 ml triphenylphosphite (0.0685 mol) in 90 ml of methylene chloride, cooled at −15° C., until a permanent yellow solution was obtained.

The chlorine excess was then eliminated by adding 0.4 ml of triphenylphosphite (0.0015 mol). A solution of 13.58 g of the product L (0.02 mol) in 15 ml of methylene chloride was added to the obtained solution containing about 0.070 mol of the triphenylphosphite-chlorine complex. A solution of 5.5 ml of pyridine was then slowly added thereto. 19 ml of isobutanol was then slowly added after having left the reaction mixture under stirring for an hour at −15° C.

HCl gas was insufflated into the mixture after an hour from the end of the addition obtaining the precipitation of the title product. The precipitated solid was filtered, rinsed with methylene chloride and dried.

The obtained product was a white microcystalline solid (7.0 g, 0.016 ml); the $^1$H-NMR data were coincident to the ones of the true product reported in literature. The molar yield, calculated on the basis of the HPLC title, was 80% on the recovered product.

EXAMPLE 16

Preparation of the diphenylmethyl 7-β-amino-3-chloro-3-cephem-4-carboxylate hydrochloride (VIII)

Chlorine gas was insufflated in a solution of 13.10 ml of triphenylphosphite (0.0485 mol) in 90 ml of methylene chloride, cooled at −15° C. until a permanent yellow solution was obtained. The chlorine excess was then eliminated by adding 0.4 ml of triphenylphosphite (0.0015 mol). A solution of 13.26 g of the product F (0.002 mol) in 15 ml of methylene chloride was added to the solution obtained containing about, 0.0050 mol of the triphenylphosphite-chlorine complex.

A solution of 4.0 ml of pyridine in 16 ml of methylene chloride was then slowly added thereto. 19 ml of isobutanol were slowly added after having left the reaction mixture under stirring for an hour at −15° C. HCl gas was insufflated into the mixture after an hour from the end of the addition, obtaining the precipitation of the title product. The precipitated solid was filtered, rinsed with methylene chloride and dried.

The product obtained was a white microcrystalline solid (7.4 g, 0.017 mol); the $^1$H-NMR data were coincident to the ones of the true product as reported in literature. The molar yield calculated on the basis of the HPLC tittle was 85% on the recovered product. EXAMPLE 17

Preparation of the 7-β-(4-carboxybutanamido)-3-hydroxymethyl-3-cephem-4-carboxylic acid (B)

1 l of a 25 mM aqueous solution of $KH_2PO_4$ containing 25 g of the 7-β-(4-carboxybutanamido)-3-acetoxymethyl-3-cephem-4-carboxylic acid (A) (0.065 mol) was carried to pH=7.5 by KOH.

Thermostating at 20° C. and adding 75 g of the acetylesterase enzyme supported on a resin, were effected.

The admixture was put under stirring for 45 minutes maintaining at pH=7 by adding a solution of 7% $NH_4OH$.

The enzyme was filtered and the solution carried at pH=6.5 with 12% HCl.

A solution containing 21.7 g of the compound B was obtained.

The yield in the solution, calculated by HPLC, was 97%.

The title product was not isolated because the solution was used in the next step.

EXAMPLE 18

Preparation of the diphenylmethyl 7-β-[(4-diphenylmethoxycarbonyl)-butanamido]-3-hydroxymethyl-3-cephem-4-carboxylate (C).

The procedure described below comprises the extractive esterification of the 7-β-(4-carboxybutanamido)-3-hydroxymethyl-3-cephem-4-carboxylic acid (B) and the isolation of the corresponding title diphenylmethyl ester. 36.9 g of diphenyldiazomethane in ethyl acetate solution were added to the solution containing 21.7 g of the compound B (0.063 mol).

The biphasic mixture was put under stirring thermostating at 10° C.

18% HCl was slowly added dropwise till pH=2–2.5, carrying on for 4 hours, maintaining the pH constant.

After completing the synthesis, the phases were separated, the organic phase being treated with 500 ml of $H_2O$, and bringing the pH at 6.5 with $Na_2CO_3$. The phases were separated rinsing the organic phase two times with a NaCl saturated solution. The organic phase was dried with $Na_2SO_4$ and the solvent was eliminated under vacuum (40 torr) at 20° C.

The oily crude product was purified by treatment with a 1:9 ethyl acetate/n-pentane mixture.

25.7 g of a white solid recognized as the title product, having a HPLC purity of 90%, were obtained. $^1$H-NMR ($CDCl_3$, 200 MHz) 2.00 (m,2H,—$CH_2$—);2.25 (t, 2H, —CH$_2$—); 2.5 (t. 2H. —CH$_2$—); 3.55 (s. 2H. C-2); 3.95+4.4 (ABq. 2H. J=12.8 Hz. CH$_2$—OH); 4.9 (d. 1H. J=4.8 Hz. C-6); 5.9 (dd. 1H. J=4.8+8.8 Hz. C-7); 6.2 (d. 1H. J=8.8 Hz. NH); 6.9 (s. 1H. diphenylmethyl-CH); 6.94 (s. 1H. diphenylmethyl-CH); 7.2+7.4 (brs. 20H. aromatic).

EXAMPLE 19

Preparation of the diphenylmethyl 7-β-[(4-diphenylmethoxycarbonyl)-butanamido]-3-chloromethyl-3-cephem-4-carboxylate (D).

10 g (0.015 mol) of the compound C obtained in the foregoing example were dissolved in 70 ml of anhydrous CH$_2$Cl$_2$, lowering the temperature at −30° C. 3.9 g (0.02 mol) of PCl$_5$ were inserted in the flask. The disappearing of the compound C was observed by HPLC after 30 minutes. 2.6 ml (0.02 mol) of triethylamine were dropwise added, leaving under stirring for 30 minutes. The reaction was estinguished with 77 ml of H$_2$O.

The phases were separated, and washing of the organic phase for two times with a NaCl saturated solution, was effected.

The solvent was eliminated under vacuum after having been dried on Na$_2$SO$_4$. The crude product was purified with cyclohexane. 9.2 g of the title product were recovered.

The molar yield was 94% on the basis of the HPLC title. $^1$H-NMR (CDCl$_3$, 200 MHz) 2.00 (m, 2H.—CH$_2$—); 2.25 (t. 2H.—CH$_2$—); 2.5 (t. 2H.—CH$_2$—); 3.42+3.52 (ABq. 2H. J=18.7 Hz. C-2); 4.4 (s. 2H. CH$_2$—Cl); 5.00 (d. 1H. J=4.8 Hz. C-6); 5.85 (dd. 1H. J=4.8+8.9 Hz.C-7); 6.2 (d. 1H. J=8.9 Hz. NH); 6.9 (s. 1H. diphenylmethyl-CH); 7.00 (s. 1H. diphenylmethyl-CH); 7.2+7.5 (brs. 20H. aromatic).

EXAMPLE 20

Preparation of the diphenylmethyl 7-β-[(4-diphenylmethoxycarbonyl)-butanamido]-3-methylene-cepham-4-carboxylate (E).

A solution of 6.94 g of the compound D obtained in the foregoing example (0.01 mol) in 80 ml of absolute, was added to a suspension of 12.5 g of activated Zn in powder, 10 g of NH$_4$Cl and 7 g of ZnCl$_2$ in 80 ml of absolute dimethylformamide cooled at −45° C.

After 3 hours under vigorous stirring at −40° C., the suspension was filtered and the solid washed with 100 ml of ethyl acetate which were added to the filtrate.

200 ml of an aqueous solution of 18% NaCl were added to the resulting solution, stirring for 30 minutes at room temperature. The organic phase was subsequently washed for two times with 100 ml of an aqueous solution of 18% NaCl, dried with Na$_2$SO$_4$, evaporating the solvent and crystallizing the resulting oil from CH$_2$Cl$_2$/n-pentane.

4.6 g of a light yellow solid, recognized as the title product, were obtained. HPLC purity=90%

NMR (CDCl$_3$, 200 MHz) 1.98 (m. 2H. —CH$_2$—); 2.23 (t, 2H, —CH$_2$—); 2.5 (t. 2H. —CH$_2$—); 3.09+3.50 (ABq. 2H. J=13, 9Hz.C-2); 5.21+5.24 (s. 2H. C$_3$=CH$_2$); 5.32 (s. 1H. C-4); 5.35 (d.1H. J=4.3 Hz.C-6); 5.64 (dd. 1H. J=4.3+9.2 Hz. C-7); 6.10 (d. 1H. J=9.2 Hz. NH); 6.86+6.88 (s. 2H. diphenylmethyl-CH); 7.23+7.37 (brs. 20H. aromatic).

EXAMPLE 21

Preparation of the diphenylmethyl 7-β-[(4-diphenylmethoxycarbonyl)-butanamido]-3-hydroxy-3-cephem-4-carboxylate (F).

Ozone (0.75 mmol 0.3/min) was insufflated for about 20 minutes into a solution of 6.60 g of the compound E obtained in the foregoing example (0.01 mol) in 160 ml of CH$_2$Cl$_2$ and 40 ml of CH$_3$OH, cooled at −75° C. After said time, the reaction mixture developed a light blue colour. The ozone excess was removed insufflating O$_2$ for 5 minutes and N$_2$ for 15 minutes.

19 g of sodium metabisulfite were added thereto, the mixture being stirred for 30 minutes at −75° C. and for about an hour at 0° C. After said time, the suspension gave a negative response to the peroxide test (KI-soluble starch).

The liquid phase was decanted and rinsed with water.

The organic phase, after drying with Na$_2$SO$_4$ and evaporating the solvent, gave an amorphous solid recognized as the title product. Purity (HPLC)=80%.

$^1$H-NMR (CDCl$_3$, 200MHz) 2.00 (m.2H.—CH$_2$—); 2.28 (t.2H.—CH$_2$—); 2.52 (t. 2H.—CH$_2$—); 3.27+3.48 (ABq. 2H. J=13.9 Hz. C-2); 5.01 (d. 1H. J=4.5 Hz. C-6); 5.71 (dd. 1H. J=4.5+8.5 Hz. C-7); 6.26 (d. 1H. J=8.5 Hz. NH); 6.87+6.89 (s. 2H. diphenylmethyl-CH); 7.23+7.37 (brs. 20H. aromatic).

We claim:

1. The compound of formula:

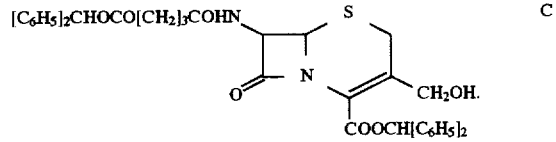

2. The compound of formula:

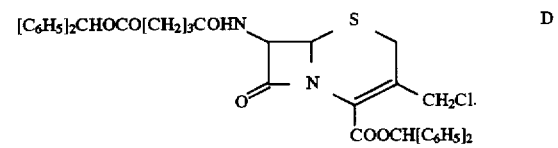

3. The compound of formula:

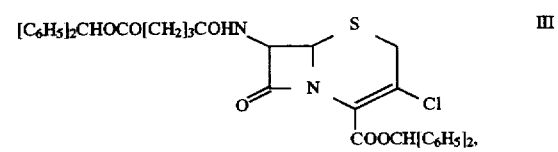

4. The compound of formula:

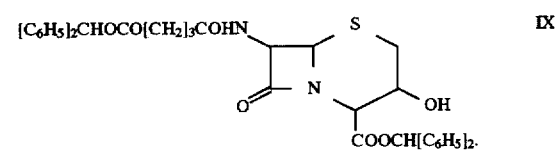

5. The compound of formula:

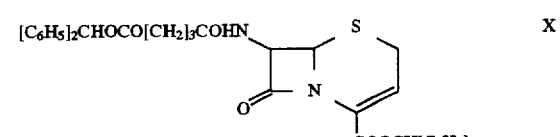

* * * * *

UNITED STATES PATENT AND TRADEMARK OFFICE
CERTIFICATE OF CORRECTION

PATENT NO. : 5,750,682
DATED : May 12, 1998
INVENTOR(S) : Loris SOGLI, et al.

It is certified that error appears in the above-identified patent and that said Letters Patent is hereby corrected as shown below:

On the title page item [30], Second Foreign Application Priority Data is incorrect, it should read:

--Jul. 22, 1994 [IT] ITALY     MI94A1562--

Signed and Sealed this

Third Day of November, 1998

Attest:

BRUCE LEHMAN

*Attesting Officer*             *Commissioner of Patents and Trademarks*